United States Patent [19]

Holzner, Sr.

[11] Patent Number: 4,931,224

[45] Date of Patent: Jun. 5, 1990

[54] AIR FRESHENER

[75] Inventor: Charles R. Holzner, Sr., Chicago, Ill.

[73] Assignee: Steiner Company, Inc., Chicago, Ill.

[21] Appl. No.: 349,522

[22] Filed: May 9, 1989

[51] Int. Cl.$^5$ .............................................. B01F 3/04
[52] U.S. Cl. ...................................... 261/30; 239/57;
422/124; 261/DIG. 65
[58] Field of Search ......................... 261/DIG. 65, 30;
222/325; 239/57; 422/124

[56] References Cited

U.S. PATENT DOCUMENTS

| | | | |
|---|---|---|---|
| 3,990,848 | 11/1976 | Corris | 239/57 |
| 4,035,451 | 7/1977 | Tringali | 261/30 |
| 4,391,309 | 7/1983 | Steiner | 141/18 |
| 4,429,812 | 2/1984 | Steiner et al. | 141/18 |
| 4,611,730 | 9/1986 | Ikesue et al. | 222/325 |
| 4,743,406 | 5/1988 | Steiner et al. | 261/30 |
| 4,840,770 | 6/1989 | Walz et al. | 261/30 |

*Primary Examiner*—Tim Miles
*Attorney, Agent, or Firm*—Emrich & Dithmar

[57] ABSTRACT

A battery operated air freshener with a housing having means for mounting the air freshener to a surface such as a wall. A motor inside the housing is electrically connected to a fan and to a battery. A replaceable cartridge with vents defining an air flow path carries a deodorizing substance and a battery. The replaceable cartridge having a receptacle is positioned within the housing such that the battery carried by the cartridge fits between spaced electrical contacts connected to the motor and hence to the fan resulting in air flow through the deodorizing substance. An anti-bootleg device in the housing has at least one prong extending into the cartridge receptacle, whereby a cartridge having an appropriate receptacle to receive the anti-bootleg device fits within the housing such that the battery carried by the cartridge fits between the spaced electrical contacts thereby establishing an electrical circuit to operate the fan. But an anti-bootleg device in the housing with a cartridge without the appropriate receptacle precludes the battery carried by the cartridge from fitting between the spaced electrical contacts and the electrical circuit is not completed rendering the air freshener inoperative.

25 Claims, 3 Drawing Sheets

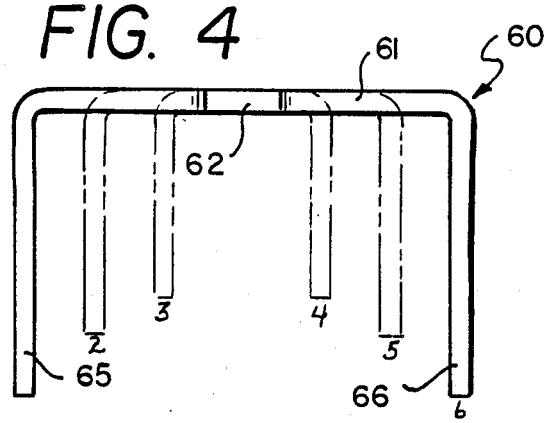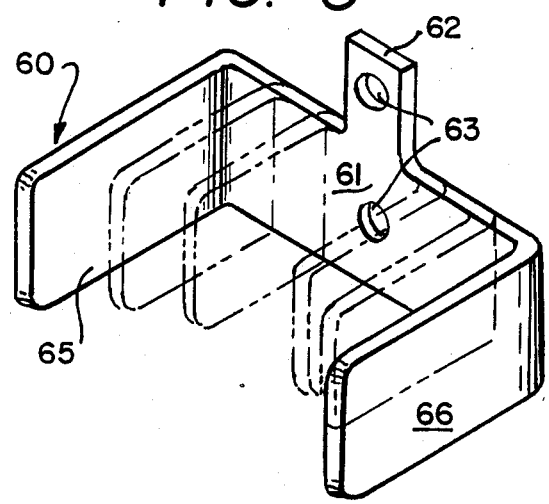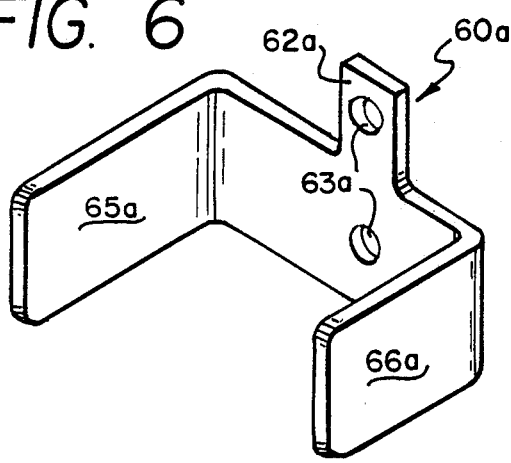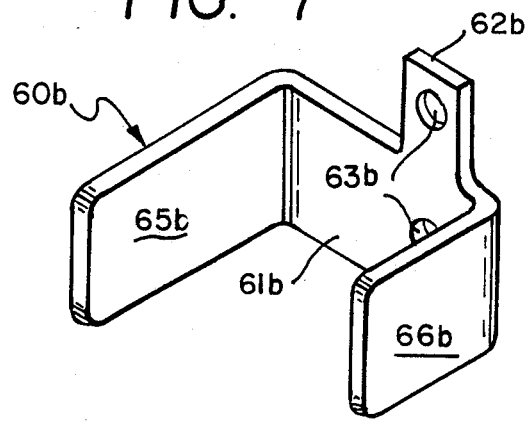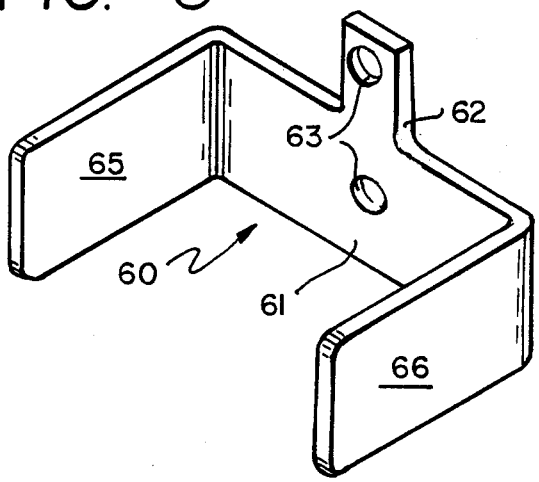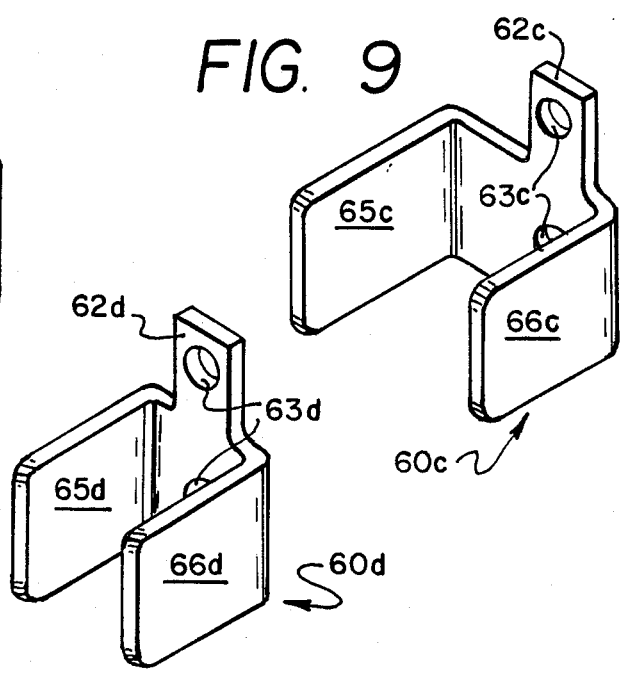

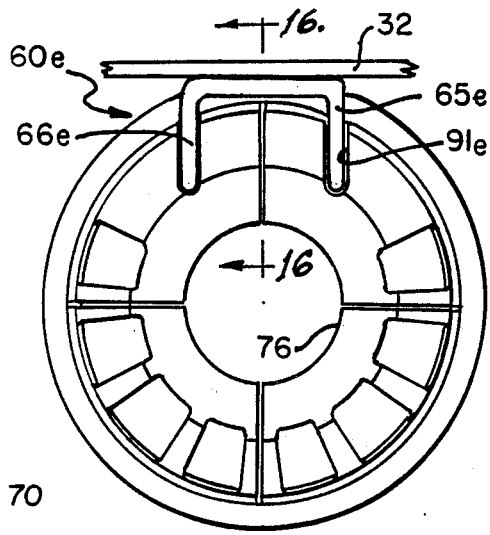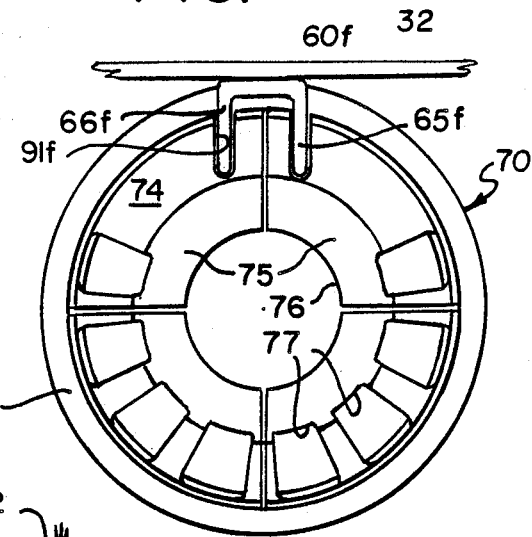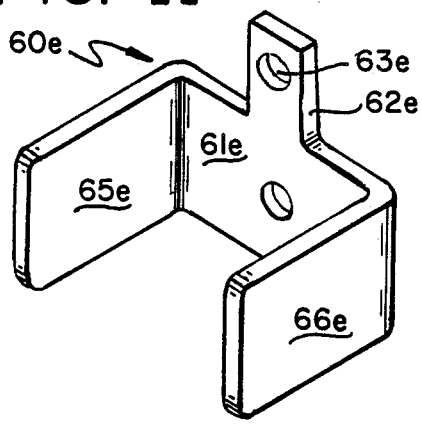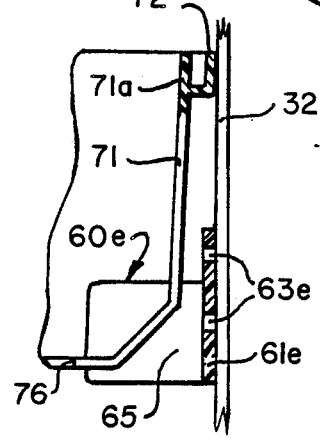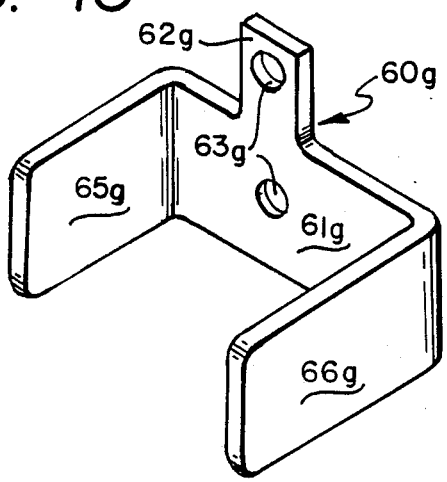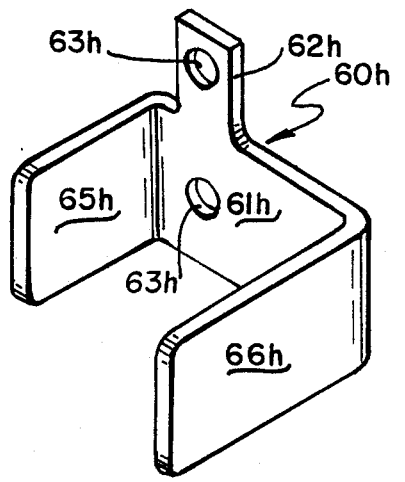

AIR FRESHENER

BACKGROUND OF THE INVENTION

This invention relates in general to air freshening or deodorizing devices and, in particular, to a self-contained air freshener which draws ambient air through the apparatus, and about or through a deodorizing cartridge to vaporize materials contained in the cartridge for distribution into the air flow.

More specifically, but without restriction to the particular embodiment and/or use which is shown and described for purposes of illustration, this invention relates to a self-contained air freshener utilizing a replaceable cartridge containing or formed from a vaporizable material, and a replaceable battery power source. These replaceable or expendable items are carried within the apparatus to permit the convenient and selective replacement of these items when necessary.

The air freshening or deodorizing device as set forth in U.S. Pat. No. 4,743,406, the disclosure of which is incorporated herein by reference, is a satisfactory commercial device. However, a problem that is inherent in this field is the use of unauthorized replacement cartridges in the dispensers. To avoid unauthorized cartridges being used in dispensers, there should be included in the dispenser some mechanism to prevent the use of unauthorized cartridges therein. In the soap dispensing field, there have been what is called anti-bootleg devices incorporated in soap dispensers, for instance see Steiner et al. U.S. Pat. No. 4,391,309 and 4,429,812, which disclose anti-bootleg devices in soap dispensers. However, in the present air freshening or deodorizing art, there is no mechanism present which would prevent the use of unauthorized cartridges in the devices.

The present invention is constructed such that the important commercial features of the device illustrated in the '406 patent are retained with the addition of anti-bootleg structure for preventing unauthorized cartridges from being used in the device.

SUMMARY OF THE INVENTION

It is therefore an object of this invention to provide an improved self-contained air freshening or deodorizing device.

Another object of this invention is to utilize a anti-bootleg device within the air freshener which prevents the use of unauthorized cartridges.

Yet another object of the invention is to provide in combination, an air freshener housing having mounted therein motor means operatively connected to a fan, a replaceable cartridge carrying a deodorizing substance positionable within the housing, anti-bootleg means fixedly positioned within the housing to intrude into the space occupied by the replaceable cartridge, and receptacle means on the cartridge complimentary in shape to the anti-bootleg means permitting insertion of a cartridge into the housing, whereby cartridges without the receptacle means being prevented from fitting within the housing by the anti-bootleg means.

Another object of the invention is to provide a battery operated air freshener comprising a housing having mounting means for mounting the air freshener to a surface, motor means inside the housing electrically connected to a fan and having spaced electrical contacts for connection to a battery, a replaceable cartridge having vents defining an air flow path and receiving therein a deodorizing substance and a battery, the replaceable cartridge being positioned within the housing such that the battery carried by the cartridge fits between the spaced electrical contacts causing rotation of the fan resulting in air flow through the vents and through the deodorizing substance, receptacle means in the cartridge, and an anti-bootleg device mounted in the housing having at least one prong extending into the cartridge receptacle means, whereby a cartridge having receptacle means receiving therewithin a prong from the anti-bootleg device fits within the housing such that the battery carried by the cartridge fits between the spaced electrical contacts thereby establishing an electrical circuit to operate the fan, the anti-bootleg device being positioned in the housing such that a cartridge without the appropriate receptacle is precluded from fitting and the battery carried by the cartridge does not fit between the spaced electrical contacts and the electrical circuit is not completed rendering the air freshener inoperative.

Another object of the invention is to provide a self-contained air freshening or deodorizing apparatus containing a two-part housing including a mounting section for securing the apparatus in an operative position and a closure section for connection to the mounting section for forming an enclosure, mounting means operatively connected to the mounting section for fastening the mounting section to a supporting surface, the mounting section including releasable coupling means engageable with the closure section to releasably connect the mounting section and the closure section forming an enclosure, anti-bootleg means fixedly located inside the enclosure having a prong extending therefrom, a battery-powered fan supported within the closure section for generating a path of air flow through the enclosure, and air freshening or deodorizing means having a receptacle shaped to receive the prong supplying a source of vaporizable material to the path of air flow, the air freshening or deodorizing means being carried within the closure section such that the prong of the anti-bootleg means fits within the receptacle and the battery-powered fan and the air freshener or deodorizing means being removable from the mounting section with the closure section to facilitate servicing.

A final object of the invention is to provide a disposable air freshening or deodorizing cartridge for use in supporting a battery within a self-contained air freshener apparatus comprising a cylindrical outer wall and a battery positioning cylindrical inner wall positioned concentrically within the outer wall, spacer means extending transversely between and connected to one end of the outer wall and the adjacent end of the inner wall for concentrically spacing the inner and outer walls one from the other forming an opening for an air passageway therebetween, a battery support ring positioned at the other end of the battery positioning inner wall, the battery support ring extending a width sufficient to form at least a partial closure of the other end of the battery positioning inner wall, and aperture means in the outer wall and in the battery support ring for receiving an anti-bootleg device carried by an associated air freshener.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

FIG. 4 is a top plan view of the anti-bootleg device useful in the present invention showing prongs 1 and 6 in full line and prongs 2-5 in phantom line;

FIG. 5 is a perspective view of the device illustrated in FIG. 4;

FIG. 6 is a perspective view of an anti-bootleg device having prongs 1 and 5;

FIG. 7 is a perspective view of an anti-bootleg device having prongs 1 and 4;

FIG. 8 is a perspective view of an anti-bootleq device having prongs 1 and 6;

FIG. 9 is a perspective view of an anti-bootleg device having prongs 2 and 4;

FIG. 10 is a perspective view of an anti-bootleg device having prongs 3 and 5;

FIG. 11 is a perspective view of an anti-bootleg device having prongs 2 and 5;

FIG. 12 is a perspective view of an anti-bootleg device having prongs 3 and 4;

FIG. 13 is a perspective view of an anti-bootleg device having prongs 2 and 6;

FIG. 14 is a perspective view of an anti-bootleg device having prongs 3 and 6;

FIG. 15 is a bottom view of a cartridge having an appropriate receptacle to receive therein the anti-bootleg device having prongs 2 and 5 as illustrated in FIG. 11;

FIG. 16 is an inverted sectional view of the cartridge and anti-bootleg device illustrated in FIG. 15 as seen along line 16—16 thereof; and FIG. 17 is a bottom view of a cartridge having a receptacle adapted to receive an anti-bootleg device having prongs 3 and 4 as illustrated in FIG. 12.

DESCRIPTION OF THE PREFERRED EMBODIMENT

Figure 1:
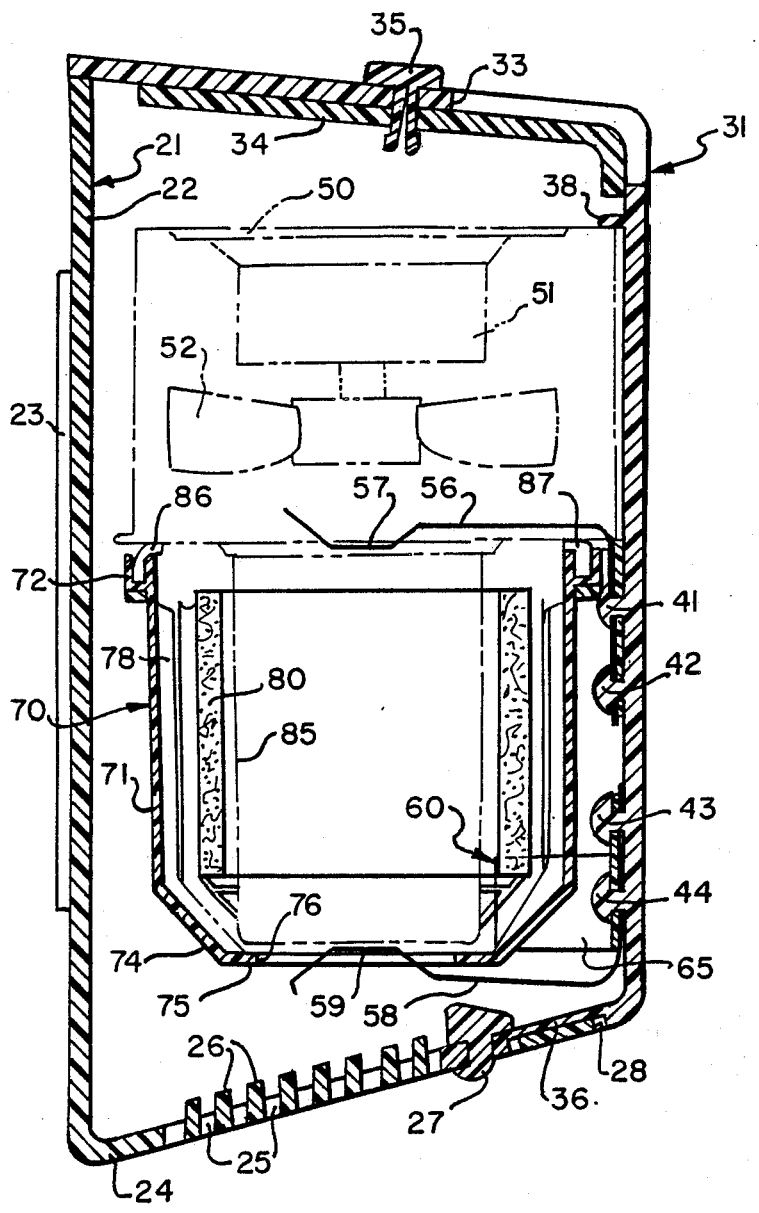
FIG. 1 is an enlarged, cross-sectional view of an air freshening device incorporating the anti-bootleg means of the invention.

Referring to FIG. 1, there is disclosed a self-contained air deodorizing device 20 which is formed in a substantially rectangular shape. The deodorizing device 20 includes a two part housing consisting of a mounting section 21 and a closure section 31, the mounting section 21 having a rectangularly shaped back wall 22 to which is secured an adhesive 23 for mounting the deodorizer 20 to a surface such as a wall. It should be understood that the deodorizer 20 may also be mounted by screws or other well known mechanism but for purposes of illustration the adhesive strip 23 is illustrated. The mounting section 21 includes an upwardly inclined bottom wall 24 having a plurality of slots 25 therein which are overlaid by louvers 26 having control means 27 for moving the louvers into and out of registry with the slots 25 in the bottom wall so as to vary the amount of air flow through the deodorizer 20, the bottom wall 24 terminating in a front edge 28.

The closure section 31 fits over the mounting section 21 and forms an enclosure therewith has a vertically disposed front wall 32 and a top wall 33 having a vent plate 34 and a vent control 35 for moving the vent plate into outer registry with a plurality of apertures (not shown) in the top wall 33, again to provide variable air flow through the deodorizer 20. The front wall 32 has an inwardly extending tang 36 which in use cooperates with an opening in the bottom wall 24 to maintain the closure section 31 on the mounting section 21, as before described in the '406 patent. Interior of the deodorizer 20 is an upper guide 38 which extends the width of the deodorizer 20 and extends inwardly from the front wall 32 of the closure section 31. A plurality of tabs extend inwardly of the front wall 32 and are integral therewith, each of the tabs 41-44 having an enlarged head or boss for a purpose hereinafter set forth. The tabs 41-44 being vertically displaced with respect to each other.

The deodorizer 20 also includes a fan shroud 50 which is cylindrical in shape mounted on the upper guide 38 and serves to house a motor 51 connected to a fan blade 52 all as previously disclosed in the 406 patent. Connected to the motor 51 by leads (not shown) is an upper bracket 56 which is fixedly connected to the front wall 31 by means of the stud tabs 41 and 42, the upper bracket 56 having a contact portion 57, for a purpose hereinafter explained. A lower bracket 58, also connected to the motor 51 by leads (not shown), is fixedly maintained on the front wall 32 by means of the stud tabs 43 and 44, the lower bracket 58 having a contact portion 59 for a purpose to be explained.

An anti-bootleg device 60 is fixedly positioned on the front wall 32 by means of the lower stub tabs 43 and 44, the enlarged heads or bosses of each of the tabs fixedly mounting the anti-bootleg device 60 to the front wall and preventing same from being dislodged without dislodging the lower bracket 58 which would render the deodorizer 20 inoperable. The anti-bootleg device 60 is best illustrated in its various embodiments in FIGS. 4-14 and includes a flat base member 61 having an upstanding tang 62 into which is drilled or punched an aperture 63. Another aperture 63 is vertically displaced from the aperture in the tang 62 and is vertically aligned therewith. The base 61 is integral with a pair of prongs 65 and 66 extending approximately perpendicularly from the base 61, the prongs 65 and 66 being best illustrated in FIGS. 4 and 5 of the drawings. FIGS. 4 and 5 of the drawings show in solid lines a anti-bootleg device 60 having solid line prongs identified as numbers 1 and 6 and in phantom line alternate embodiments of the anti-bootleg device 60 with prongs 2, 3 4 and 5 (in phantom) being positioned as illustrated. With the anti-bootleg device 60 of the present invention, various combinations of prongs 1-6 may be used to provide different anti-bootleg devices such that various customers may have anti-bootleg devices which are individualized and will not accept cartridges as will be explained, except for those that are particularly adapted for the specific combination of prongs 1-6 in the anti-bootleg device 60 in the dispenser.

Figure 3:
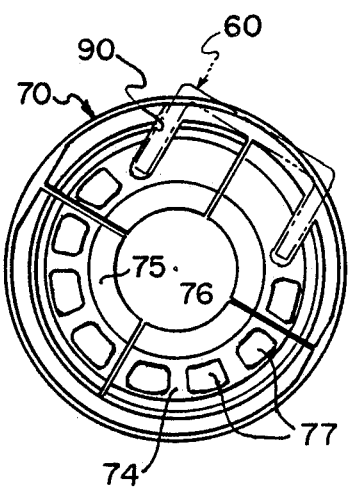
FIG. 3 is a bottom view of the cartridge illustrated in FIG. 2.

Referring now to FIGS. 1 and 3, there is illustrated a cartridge 70 which is particularly adapted to receive therein the prongs of the docking device illustrated in FIGS. 4 and 8, that is a 1–6 docking device. Cartridge 70 includes an outer cylindrical wall 71 provided with an annular lip 72 spaced from the upper portion 71a of the annular wall 71 defining a channel 73 between the annular lip 72 and the upper portion 71a of the cylindrical wall 71. A frustoconical portion 74 extends inwardly from the wall 71 and joins at the bottom end with a flat bottom wall 75 which has a central aperture 76 therein. A plurality of radially spaced vents 77 are molded or punched in the frustoconical wall portion 74 as illustrated in FIG. 3. A plurality of ribs 78 serve to strengthen the cartridge 70, as hereinafter explained.

Figure 2:
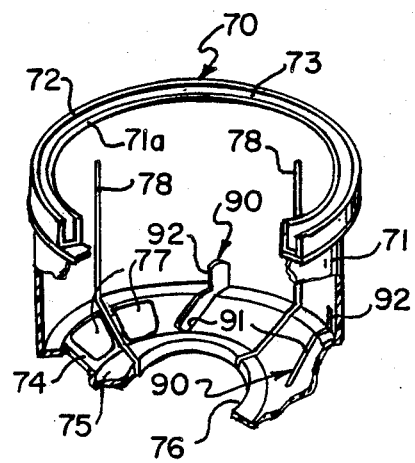
FIG. 2 is an enlarged perspective view partly broken away of a replacement cartridge for use in the air freshening device illustrated in FIG. 1.

A cylindrical well 85 is connected to a flat top member 86 having a downwardly extending lip 87 adapted to fit into the annular space 73 previously described. The well 85 forms with the adjacent wall 71 an annular space which receives a packet of vaporizable material 80, as illustrated. A battery (not shown) is positioned within the well 85 between the battery clips or brackets 56 and 58, as best seen in FIG. 1. Anti-bootleg receptacle means 90 consist of spaced apart slots having a portion 91 in the frustoconical portion 74 of the cartridge 70 and having a portion 92 in the vertical wall 71 of the cartridge. The position of the receptacle slots 90 depends upon the specific anti-bootleg device 60 which is to be received for each dispenser, the various cartridges each having receptacles 90 specifically designed to accommodate one of the various prong positions illustrated in FIGS. 4–14. For instance, the cartridge 70 in FIGS. 2 and 3 have a receptacle 90 which includes two slots positioned to receive an anti-bootleg device 60 having prongs 1 and 6. An anti-bootleg device such as illustrated in FIG. 7 having prongs 1 and 4 will preclude a cartridge such as illustrated in FIGS. 2 and 3 from fitting in a deodorizer dispenser 20 so that the battery 95 will not fit between the brackets 56 and 58 and no electrical circuit will be established if the receptacle 90 in the cartridge 70 is not of a type which will accommodate a specific anti-bootleg device 60 in the deodorizer dispenser 20.

As best seen in FIGS. 4 and 5, the anti-bootleg device 60 includes a two prong device which is any combination of the six prongs illustrated, provided that one prong is on each side of the aperture 63. For instance, FIG. 6 illustrates an anti-bootleg device 60a in which prongs 1–5 are selected, that is prongs 65a and 66a are selected. In a dispenser 20 having a bootleg device such as 60a illustrated in FIG. 6 the only cartridge 70 which would be acceptable in the dispenser is one having receptacles 90 with the slots therein spaced to receive the two prongs 65a and 66a.

Referring to FIG. 7 there is illustrated an anti-bootleg device 60b which is a 1–4 device that is with prongs 65, 66 numbered 1,4 in FIG. 4, it should be understood that device 60b has prongs with a different spacing than device 60a, and it should be noted that prongs 1–6 have a different longitudinal extent than prongs 2–5 which have a different longitudinal extent than prongs 3–4. By virtue of the different lengths, the slots 90 can be customized so that various slots can be made different lengths, where required, adding an additional feature which precludes the use of unauthorized cartridges 70.

FIG. 9 shows an anti-bootleg device 60c having prongs 2,4, and FIG. 10 shows an anti-bootleg device 60d having the 3–5 prongs. Referring to FIGS. 11–14, there is disclosed therein, respectively, an anti-bootleg device 60e for a 2–5 prong device, anti-bootleg device 60f for a 3–4 prong device, anti-bootleg device 60g for a 2–6 device and finally anti-bootleg device 60h for a 3–6 device. Accordingly, it is clear that various combinations of prongs can be used to make customized anti-bootleg devices 60 which will accommodate only specifically designed cartridges 70 having slots 90 which are not only appropriately spaced but of appropriate lengths, particularly when prongs of different longitudinal extents are used.

Referring again to FIGS. 15 and 16, there is illustrated a combination receptacle 90e and an anti-bootleg device 60e, also seen in FIG. 11 using a two-five prong device. Using the appropriate receptacle 90e in combination with the anti-bootleg device 60e it will be seen that the associated cartridge 70 fits in the deodorizer dispenser 20 in a manner which permits the associated battery to make electrical contact with the upper and lower brackets 56, 58 in a manner to establish the electrical circuit to the motor 51 and the operation of the fan 52.

Similarly, FIG. 17 shows the operative association of a cartridge 70 having an anti-bootleg device 60f including prongs numbers 3 and 4 and the appropriate receptacles 90f positioned to receive the three-four prong anti-bootleg device 60f.

It is seen therefore that there has been provided a system in which each dispenser 20 has in it an anti-bootleg device 60 with a particularly chosen pair of prongs 65 and 66 which will preclude the use of any cartridge 70 except a cartridge having a corresponding receptacle pair 90 to receive the prongs. The use of unauthorized cartridges in dispensers having the anti-bootleg device of the present invention will preclude the operation of the motor 51 and fan 52 rendering the entire deodorizer inoperable.

While there has been disclosed what is considered to be the preferred embodiment of the present invention, it is understood that various changes in the details may be made without departing from the spirit, or sacrificing any of the advantages of the present invention.

I claim:

1. In combination, an air freshener housing defining an internal space, said housing having mounted therein motor means operatively connected to a fan, a replaceable cartridge carrying a deodorizing substance positionable within said housing, anti-bootleg means including spaced prongs fixedly positioned within said housing to intrude into the space occupied by said replaceable cartridge, and receptacle means on said cartridge complimentary in shape to said anti-bootleg means permitting insertion of a cartridge into said housing, whereby cartridges without said receptacle means being prevent from fitting within said housing by said anti-bootleg means.

2. The combination of claim 1, wherein said anti-bootleg means is mounted on said air freshener housing extending into said internal space formed by housing.

3. The combination of claim 2, wherein the receptacle means are in the bottom of said cartridge.

4. The combination of claim 3, wherein the receptacle means are multiple slots and said anti-bootleg means includes spaced planar prongs received in said slots.

5. The combination of claim 4, wherein said prongs extend into the side and the bottom of said cartridge.

6. The combination of claim 4, wherein said receptacle means are two slots and said anti-bootleg means includes two prongs.

7. The combination of claim 6, wherein said prongs are the same size.

8. The combination of claim 6, wherein said prongs are of different sizes.

9. The combination of claim 7, wherein said receptacle means are the same sizes.

10. A battery operated air freshener comprising a housing having mounting means for mounting said air freshener to a surface, motor means inside said housing electrically connected to a fan and having spaced electrical contacts for connection to a battery, a replaceable cartridge having vents defining an air flow path and receiving therein a deodorizing substance and a battery, said replaceable cartridge being positioned within said housing such that the battery carried by said cartridge fits between said spaced electrical contacts causing rotation of said fan resulting in air flow through said vents and through said deodorizing substance, receptacle means in said cartridge, and an anti-bootleg device mounted in said housing having at least one prong extending into said cartridge receptacle means, whereby a cartridge having receptacle means receiving therewithin a prong from said anti-bootleg device fits within said housing such that the battery carried by said cartridge fits between said spaced electrical contacts thereby establishing an electrical circuit to operate said fan, said anti-bootleg device being positioned in said housing such that a cartridge without the appropriate receptacle is precluded from fitting and the battery carried by the cartridge does not fit between said spaced electrical contacts and the electrical circuit is not completed rendering said air freshener inoperative.

11. The air freshener of claim 10, wherein said anti-bootleg device has more than one prong.

12. The air freshener of claim 10, wherein said anti-bootleg device has two prongs.

13. The air freshener of claim 10, wherein said prongs are the same size.

14. The air freshener of claim 12, wherein said prongs are different sizes.

15. The air freshener of claim 12, wherein said prongs extend into said housing.

16. The air freshener of claim 12, wherein said prongs are positioned a predetermined distance from each other to match the receptacles in said cartridges.

17. The air freshener of claim 16, wherein said anti-bootleg device is selected from a series of two prong units, each unit having two prongs differently positioned to each other to provide nine different combinations.

18. A self-contained air freshening or deodorizing apparatus containing a two-part housing including a mounting section for securing the apparatus in an operative position and a closure section for connection to said mounting section for forming an enclosure, mounting means operatively connected to said mounting section for fastening said mounting section to a supporting surface, said mounting section including releasable coupling means engageable with said closure section to releasably connect said mounting section and said closure section forming an enclosure, anti-bootleg means fixedly located inside said enclosure having a prong extending therefrom, a battery-powered fan supported within said closure section for generating a path of air flow through said enclosure, and air freshening or deodorizing means having a receptacle shaped to receive said prong supplying a source of vaporizable material to said path of air flow, said air freshening or deodorizing means being carried within said closure section such that said prong of said anti-bootleg means fits within said receptacle and said battery-powered fan and said air freshener or deodorizing means being removable from said mounting section with said closure section to facilitate servicing.

19. The self-contained air freshening or deodorizing apparatus of claim 18, wherein said air freshening or deodorizing means includes a replaceable cartridge carrying the air freshening or deodorizing means and a battery, said cartridge having a housing comprising a cylindrical outer wall and a cylindrical inner wall positioned concentrically within said outer wall defining a battery compartment within said inner wall and an annular space between said inner and outer walls for receiving the vaporizable material, spacer means extending transversely between and connected to inner and said outer walls for concentrically spacing said inner and outer walls one from the other forming an inlet for an air passageway therebetween, said cylindrical inner wall extending at one end thereof a length greater than said cylindrical outer wall, connecting means extending between said one end of said inner wall and the adjacent end of said outer wall forming a tapered end of the cartridge and an outlet for said air passageway between said inner and outer walls, said receptacle being formed in said taped end and extending into a portion of said outer wall to receive said anti-bootleg prong therein.

20. The self-contained air freshening or deodorizing apparatus of claim 19, wherein said closure section has a pair of spaced electrical contacts connected to said fan, said spaced electrical contacts being positioned to contact the positive and negative ends of a battery positioned within said cartridge only when said anti-bootleg prong fits within said cartridge receptacle means.

21. A disposable air freshening or deodorizing cartridge for use in supporting a battery within a self-contained air freshener apparatus comprising a cylindrical outer wall and a battery positioning cylindrical inner wall positioned concentrically within said outer wall, spacer means extending transversely between and connected to one end of said outer wall and the adjacent end of said inner wall for concentrically spacing said inner and outer walls one from the other forming an opening for an air passage-way therebetween, a battery support ring positioned at the other end of said battery positioning inner wall, said battery support ring extending a width sufficient to form at least a partial closure of said other end of said battery positioning inner wall, and aperture means in said outer wall and in said battery support ring for receiving an anti-bootleg device carried by an associated air freshener.

22. The disposable air freshening or deodorizing cartridge of claim 21, wherein said battery positioning cylindrical inner wall extends beyond said cylindrical outer wall and is connected thereto by a tapered wall portion, said aperture means being positioned in said outer wall, said tapered wall portion and said battery support ring.

23. The disposable air freshening cartridge of claim 22, further including a quantity of vaporizable deodorizing material carried within said cartridge between an inner surface of said outer wall and an outer surface of said inner wall in said air passageway formed between said walls.

24. The disposable air freshening cartridge of claim 23, further including a plurality of positioning ribs circumferentially spaced about the inner surface of said outer wall and extending inwardly toward the outer surface of said inner wall for positioning said quantity of vaporizable deodorizing material carried in said air passageway formed between said inner and outer walls.

25. The disposable air freshening cartridge of claim 24, wherein said plurality of positioning ribs extend outwardly from the joinder of said connecting means and said battery support ring adjacent to the outer surface of said inner wall for positioning said free end of said inner wall relative to said battery support ring and said means for receiving said anti-bootleg device is a pair of slots in said cartridge inner and outer walls.

* * * * *